United States Patent
Spino et al.

(10) Patent No.: US 9,335,242 B2
(45) Date of Patent: May 10, 2016

(54) VISCOSITY MEASUREMENT OF LIQUIDS AT SUBAMBIENT TEMPERATURES

(71) Applicant: Cambridge Viscosity, Inc., Medford, MA (US)

(72) Inventors: Larry Angelo Spino, Houston, TX (US); Daniel Alfred Airey, Woburn, MA (US); David Anthony Malaguti, Stoneham, MA (US); Herve Philippe Cleris, Curcy sur Orne (FR); Viachaslau Urvantsau, Fontenay le Marmion (FR)

(73) Assignee: Cambridge Viscosity, Inc., Medford, MA (US)

( * ) Notice: Subject to any disclaimer, the term of this patent is extended or adjusted under 35 U.S.C. 154(b) by 338 days.

(21) Appl. No.: 14/066,733

(22) Filed: Oct. 30, 2013

(65) Prior Publication Data

US 2014/0250983 A1     Sep. 11, 2014

Related U.S. Application Data

(60) Provisional application No. 61/774,226, filed on Mar. 7, 2013.

(51) Int. Cl.
  *G01N 11/00*    (2006.01)
  *G01N 11/14*    (2006.01)
  *G01N 11/16*    (2006.01)

(52) U.S. Cl.
  CPC ............... *G01N 11/14* (2013.01); *G01N 11/16* (2013.01); *G01N 2011/002* (2013.01)

(58) Field of Classification Search
  CPC . G01N 11/14; G01N 11/08; G01N 2011/002; G01N 11/04; G01N 11/10; B01L 7/02
  USPC ........................................................ 73/54.43
  See application file for complete search history.

(56) References Cited

U.S. PATENT DOCUMENTS

| | | | | |
|---|---|---|---|---|
| 4,361,008 A * | 11/1982 | Dineen | ................ | F02G 1/0435 60/520 |
| 4,676,066 A * | 6/1987 | Tailer | ................ | F02G 1/04 60/517 |
| 5,661,233 A | 8/1997 | Spates et al. | | |
| 6,463,793 B1 * | 10/2002 | Selby | ................ | G01N 11/14 73/54.26 |
| 7,614,285 B2 | 11/2009 | Airey et al. | | |
| 8,262,283 B2 | 9/2012 | Yang et al. | | |
| 2010/0006284 A1 | 1/2010 | Sonne et al. | | |
| 2010/0116034 A1 * | 5/2010 | Abbott | ................ | G01N 11/14 73/54.35 |
| 2010/0281956 A1 * | 11/2010 | Gosling | ................ | G01N 11/04 73/54.04 |
| 2012/0159943 A1 * | 6/2012 | Steiner | ................ | F02G 1/043 60/526 |

OTHER PUBLICATIONS

Herve Abdi, "The Method of Least Squares".

* cited by examiner

*Primary Examiner* — Eric S McCall
*Assistant Examiner* — Mohammed E Keramet-Amircola
(74) *Attorney, Agent, or Firm* — Gunn, Lee & Cave, P.C.

(57) ABSTRACT

An apparatus and method is shown for determining the pumpability limit, freeze point and/or pour point of liquids, particularly fuels, at sub-ambient temperatures. A sample is placed in a viscometer which viscometer is rapidly cooled by a chiller. During cooling, after some measurements of temperature and viscosity, further temperatures and viscosity are approximated using the least squares method, which temperature and viscosity are subsequently measured to determine the pumpability limit. Continuation of the method will also give the freeze point and pour point of the sample being tested.

7 Claims, 7 Drawing Sheets

VISCOSITY MEASUREMENT OF LIQUIDS AT SUBAMBIENT TEMPERATURES

CROSS REFERENCE TO RELATED APPLICATIONS

This is a formal utility patent application from Provisional Application for Patent Ser. No. 61/774,226, filed on Mar. 7, 2013.

BACKGROUND OF THE INVENTION

1. Technical Field

The present invention relates to determining characteristics of liquids at sub-ambient temperatures and, more particularly, determining the pumpability limit, freeze point, and pour point at sub-ambient temperatures.

2. Background

As commercial aircraft fly over the North Pole for the shortest routes to Europe, fuel inside of the aircraft are subject to very low temperatures. In making such flights, it is important to know the suitability of the fuel before it is loaded onto the aircraft. The flight plans of the aircraft may be altered to fly at lower altitudes, or a different route may be taken, if the fuel is not suitable for such very low temperatures as may be encountered. If it is suspected that the aircraft fuel would freeze or form solid crystals, either of which would not be amenable to optimized flow, the crew could alter the flight path so the aircraft does not experience such low temperatures. The alternate flight path could be as simple as flying at lower altitudes where the temperature is warmer.

In the past, the jet fuel was characterized by its freeze point. An aircraft would not fly in such a condition that the freeze point of the fuel is ever reached.

A few years ago, the International Air Transport Association (IATA) asked the Coordinating Research Counsel (CRC) to take a look at freeze point and determine if it was the best way to characterize the jet fuel. As a result of such research, it was determined that freeze point was probably not the best way to characterize the jet fuel at sub-ambient temperatures. The conclusion was reached that viscosity was probably a better way to characterize the jet fuel at sub-ambient temperatures.

Cambridge Viscosity, Inc., the assignee of the present patent application, manufactures and sells a viscometer as shown in U.S. Pat. No. 7,614,285, issued on Nov. 10, 2012, entitled "Dynamic Reciprocating—Bob Rheometry." The viscometer is used to measure the viscosity of all type of fluids. Viscosity of a fluid is determined by the time for a bob or piston to reciprocate in the fluid under constant magnetic force. There has not been a suggestion to use the viscometer at sub-ambient temperatures.

BRIEF SUMMARY OF THE INVENTION

It is an object of the present invention to determine characteristics of a fluid at sub-ambient temperatures.

It is another object of the present invention to use a viscometer to determine the pumpability limit, the freeze point or the pour point of a fuel at sub-ambient temperature.

It is another object of the present invention to determine the dynamic viscosity of a fluid continuously from ambient to a very low temperature using a reciprocating piston.

It is yet another object of the present invention to provide a chiller for the rapid decrease of temperature of a viscometer while continuously measuring the viscosity of a fluid in the viscometer during such rapid changes of temperature.

It is still another object of the present invention to provide a self-contained viscometer with a reciprocating piston and portable chiller that can be used to rapidly change temperature of a fluid being measured.

It is still another object of the present invention to use a viscometer and a chiller for rapid decreases or increases in temperature of a fluid being measured while determining the pumpability limit, the freeze point and/or the pour point of the fluid being tested.

The viscosity of fluids (particularly fuels) can be measured continuously from ambient to very low temperatures of less than −55° C. Dynamic viscosity of the liquid is measured using an oscillating piston measuring technique. Very low temperatures are obtained using a chiller such as a Stirling engine. Kinematic viscosity can be obtained once density of a liquid of interest is known. Viscosity as a function of temperature can be derived from the continuous viscosity/temperature data generated, and the temperature at which specific events occur (i.e. pumpability limit, pour point and/or freeze point) can be quickly ascertained. Combining the oscillating piston-type viscometer with a chiller such as a Stirling engine gives a self-contained, single component device for making viscosity measurements. The viscosity-temperature measurements can also be compared with an estimated freeze point of the particular liquid being tested.

The sample to be measured is placed in a measurement cell and the process is initiated. The measurement cell will cool rapidly along with the sample therein while measuring viscosity and temperature and storing the data in memory. A computer will dynamically analyze the data collected to calculate an approximate temperature-viscosity curve. The computer will predict the temperature of the pumpability limit by extrapolation of the approximation curve. The rate and direction of temperature change is adjusted to determine the pumpability limit for the fluid under test during the thermostatic mode. The pumpability limit is then reported to the operator.

If additional cold properties are desired, the measurement cell will continue to cool the sample while measuring viscosity and temperature and storing the data in memory. The computer will calculate the difference between the approximate viscosity curve and the measured values of viscosity. The computer will also calculate the second derivative of the difference between the measured viscosity minus the approximated viscosity with respect to temperature.

The rate and direction of temperature change is used to determine the point where the second derivative changes from the approximated value. The operator will continue to adjust the direction and rate of the temperature change to determine the moment the piston is blocked. Then, the freeze point and the pour point temperatures are calculated based upon these characteristic temperatures. Again, the cold properties of the freeze point and the pour point are reported to the operator. Thereafter, the measuring cell is returned to ambient temperature, the sample being tested is cleaned out, a new sample inserted and a new test begun.

DETAILED DESCRIPTION OF AN ILLUSTRATED EMBODIMENT

Figure 1:
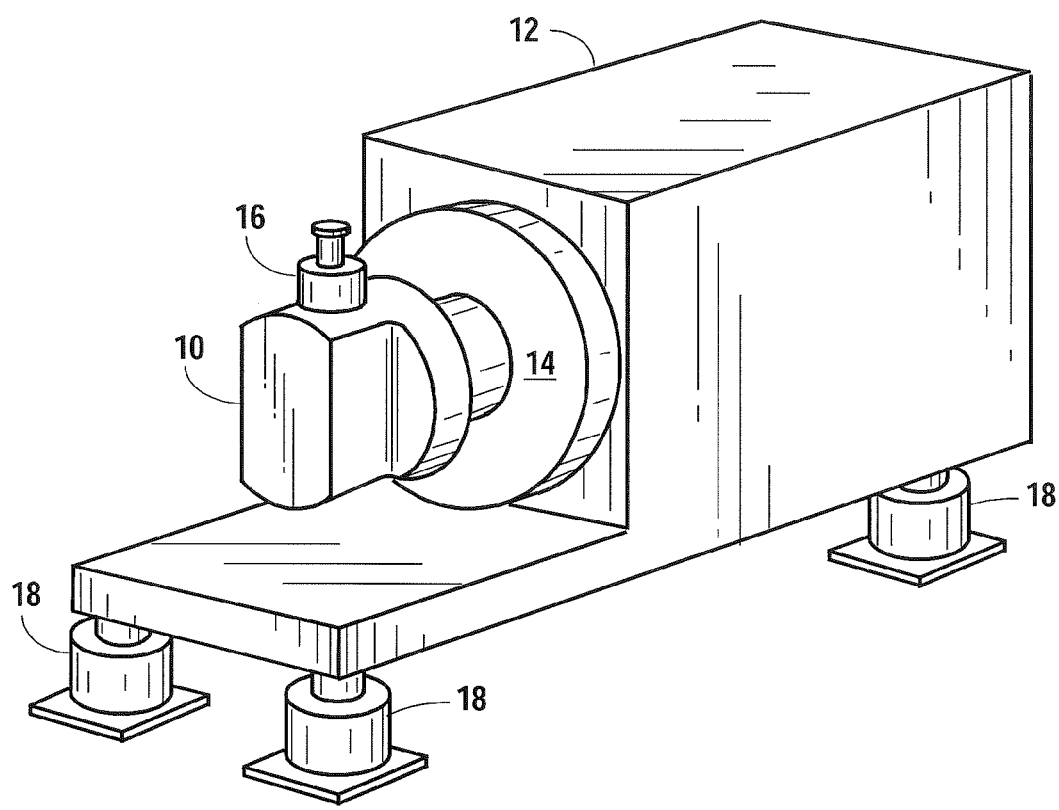
FIG. 1 is a perspective view of a viscometer and chiller.

Referring to FIG. 1, a viscometer 10 is shown attached to a chiller 12 that has an array of fins 14 for shedding heat from the viscometer 10. The viscometer 10 has a sealing cover 16 through which a fluid to be measured can be inserted.

While the chiller 12 may be of any particular type, a Stirling engine was found particularly suitable as a chiller. If a Stirling engine is used, then dampeners 18 may be located below the chiller 12 to dampen out the vibrations.

Figure 3:
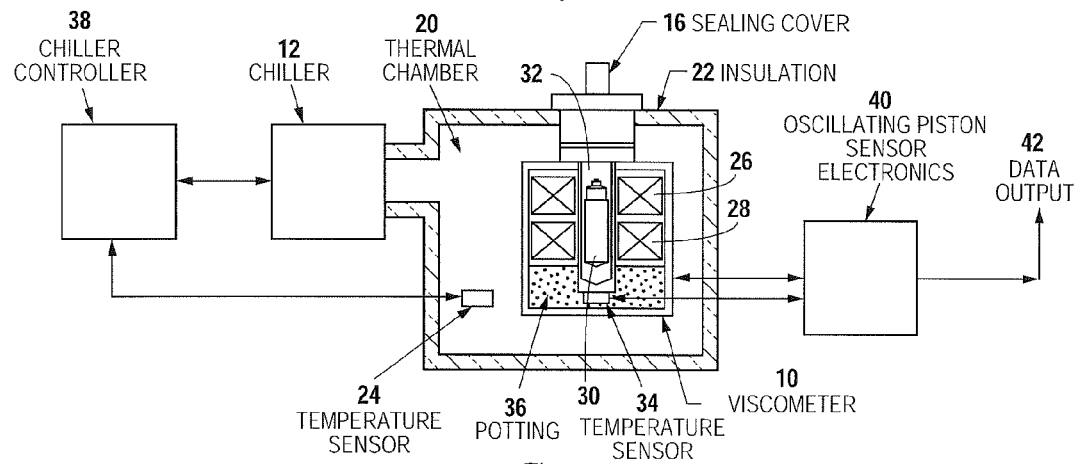
FIG. 3 gives a cross-section of the viscometer with block representations of the cooling and the electronics.

Referring to FIG. 3, the sealing cover 16 is shown for the viscometer 10. The viscometer 10 is contained inside of a thermal chamber 20 which is contained inside of insulation 22. A temperature sensor 24 determines the temperature inside of the thermal chamber 20.

Within the viscometer 10 are coils 26 and 28, one of which is used to drive the oscillating piston 30. The other coil 26 or 28 measures the position of the oscillating piston 30.

By removing the sealing cover 16, a fluid to be tested is injected into the oscillating piston chamber 32. Assuming that coil 26 is driving the oscillating piston 30 upward, coil 28 will be measuring the position of the oscillating piston 30 in the oscillating piston chamber 32. Upon oscillating piston 30 reaching the uppermost position, the coils switch their function so that coil 28 will now drive the oscillating piston 30 downward and coil 26 will measure the position of the oscillating piston 30. The oscillating piston 30 contains ferromagnetic materials therein so the oscillating piston 30 can be magnetically driven back and forth in the oscillating piston chamber 32. At the same time, the oscillating piston 30 must be resistant to corrosion. An oscillating piston 30 could be made of stainless steel and impregnated with ferromagnetic material.

The lower part of the viscometer 10 has another temperature sensor 34 below the piston chamber to more accurately measure the temperature of the fluid contained within the oscillating piston chamber 32. The temperature sensor 34 is held in position along with the oscillating piston chamber 32 by thermally conductive potting 36. A good description of the operation of the viscometer 10 is contained in U.S. Pat. No. 7,614,285, which is hereby incorporated by reference.

To raise and lower the temperature of the thermal chamber 20 and hence the viscometer 10, a chiller 12 (the same as the chiller 12 shown in FIG. 1) is thermally connected to the thermal chamber 20. A chiller controller 38, which connects to the temperature sensor 24 contained inside of the thermal chamber 20, is used to regulate the chiller 12.

Operation of coils 26 and 28 to control the motion of the oscillating piston 30 is controlled by oscillating piston sensor electronics 40. The oscillating piston sensor electronics 40 is also connected to the temperature sensor 34. Temperature sensor 34 accurately measures the temperature of the fluid under test inside of oscillating piston chamber 32. The oscillating piston sensor electronics 40 provides data output 42, which data will be discussed in more detail herein below.

Figure 2:
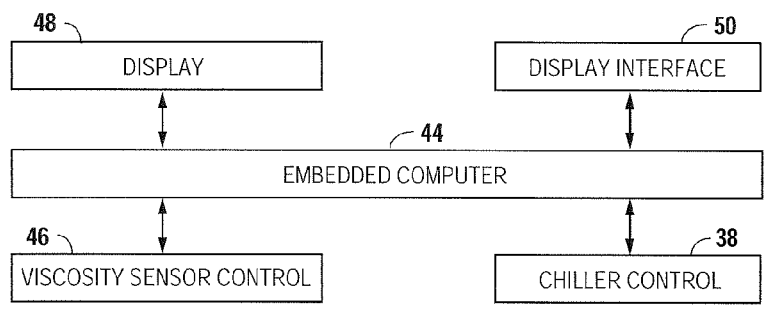
FIG. 2 is a block diagram of the controls for FIG. 1.

The entire system as shown in FIGS. 1 and 3 will have an embedded computer 44 with a viscosity sensor control 46, information from which can be seen on a display 48 as shown in FIG. 2. Also, the embedded computer 44 has the chiller controller 38 which can communicate through the display interface 50.

The oscillating piston sensor electronics 40 shown in FIG. 3 may be essentially the same as the viscosity sensor control 46 in FIG. 2 or there may be some differences. The data output 42 of FIG. 3 may be the same as the display 48 of FIG. 2, or there may be some differences. Under steady state conditions, the temperature of the temperature sensor 34 and the thermal chamber 20 will be the same temperature. The temperature sensor 34 is immediately below the oscillating piston chamber 32 to more accurately measure the temperature therein. However, during operation, temperature sensor 34 will more accurately measure the temperature of the fluid under test because of its closer proximity of the fluid under test. During normal operations, there will be some thermal lag between the temperature of the chiller 12 and the temperature sensor 34. Even the potting 36 is thermally conductive to provide for more rapid heat transfer to the oscillating piston chamber 32.

Figure 4:
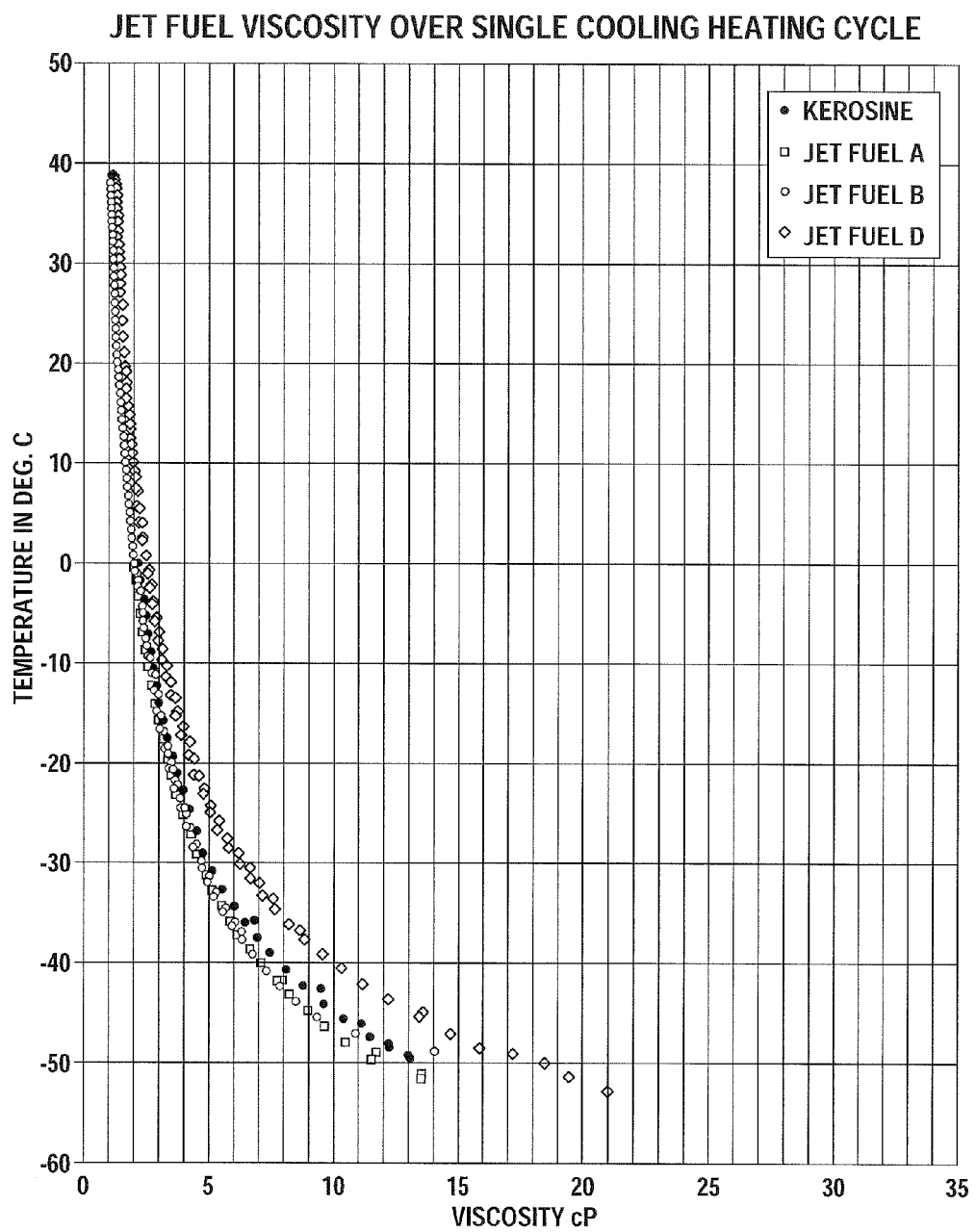
FIG. 4 is a plot of the viscosity versus temperature of various fuels.

Referring now to FIG. 4, plots are made of temperature in degrees centigrade versus the viscosity in centipoises (cP). Plotted in FIG. 4 is the temperature versus viscosity for representative samples labelled kerosene, jet fuel A, jet fuel B and jet fuel D. The beginning point of the plot is near 40° C. to approximately −50° C., at which point the sample under test begins to freeze. Many times, it is desirable to know the exact point that a fuel is no longer pumpable, freezes, or will not pour.

Figure 5:
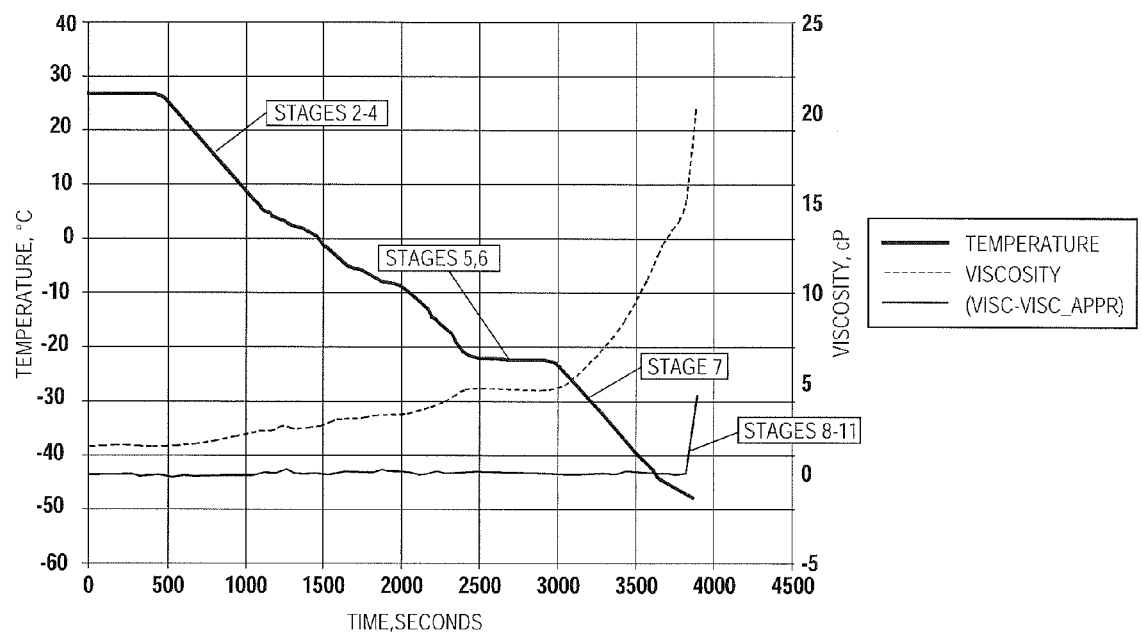
FIG. 5 is a plot of a temperature and viscosity versus time, along with the second derivative of viscosity.

Using the present invention as shown in FIGS. 1-3, assuming a fuel to be tested is placed inside of the oscillating piston chamber 32 by removing the sealing cover 16 as shown in FIG. 3. By programming the embedded computer 44 and making appropriate entries in the display interface 50, the chiller 16 may be operated in a manner as is shown in the chart on FIG. 5. Initially, the viscometer 10 is maintained at a fixed temperature for a short period of time. However, as is illustrated in the temperature plot of FIG. 5, during Stages 2-4, the temperature of the fuel sample being tested is rapidly decreased. The stages as shown in FIG. 5 are the same as the numbered stages of the flow diagram in FIG. 8. In Stage 1, the fuel under test is introduced into the oscillating piston chamber 32 and the test started. In Stage 2, the chiller will quickly cool the sample under test while measuring viscosity and temperature and storing the data in memory of the embedded computer 44.

In Stage 3, the embedded computer 44 will dynamically analyze the data collected to calculate an approximation curve of the temperature versus viscosity.

In Stage 4, the temperature of the pumpability limit is predicted by extrapolation of the approximation curve in Stage 3.

During Stages 5 and 6, the temperature of the chiller and, hence, the viscometer 10 is maintained relatively constant, or at least the rate of temperature decline is greatly reduced. During Stage 5, the rate and direction of temperature change is adjusted to determine the pumpability limit for the fuel in a thermostatic mode. In Stage 6, the pumpability limit is reported to the operator as a single number with or without a supporting chart. If the pumpability limit is all that is desired, then nothing else occurs in the test and the temperature of the viscometer 10 is returned to ambient. However, if other cold properties of the fluid under test are desired, the chiller continues in Stage 7 to quickly cool the sample under test while measuring viscosity and temperature and storing the data in memory. Simultaneous with measuring the temperature as shown in FIG. 5, the viscosity of the fluid under test is also measured.

As can be seen in FIG. 5, the second derivative of viscosity (Visc−Visc$_{appr}$) is also plotted. The difference between the approximated viscosity and the measured viscosity are essentially zero centipoise as is indicated in FIG. 5. However, at Stage 8, there starts to be a significant variation between the approximated curve for viscosity and the measured viscosity. At stage 9, the second derivative of the viscosity is calculated. Then, at Stage 10, the rate and direction of the temperature change is adjusted to determine the temperature at the moment of the change of the approximated curve from the measured values. In Stage 11, the rate and direction of temperature change is continued to be adjusted until the oscillating piston 30 no longer moves inside of the oscillating piston chamber 32. In Stage 12, the freeze point and pour point are calculated based upon the temperatures at the point of deviation between the approximated curve and the measured curve, and the temperature at the moment of piston blocking In Stage 13, the cold property values may be reported to the operator as a single number or with a supporting chart.

Figure 8:
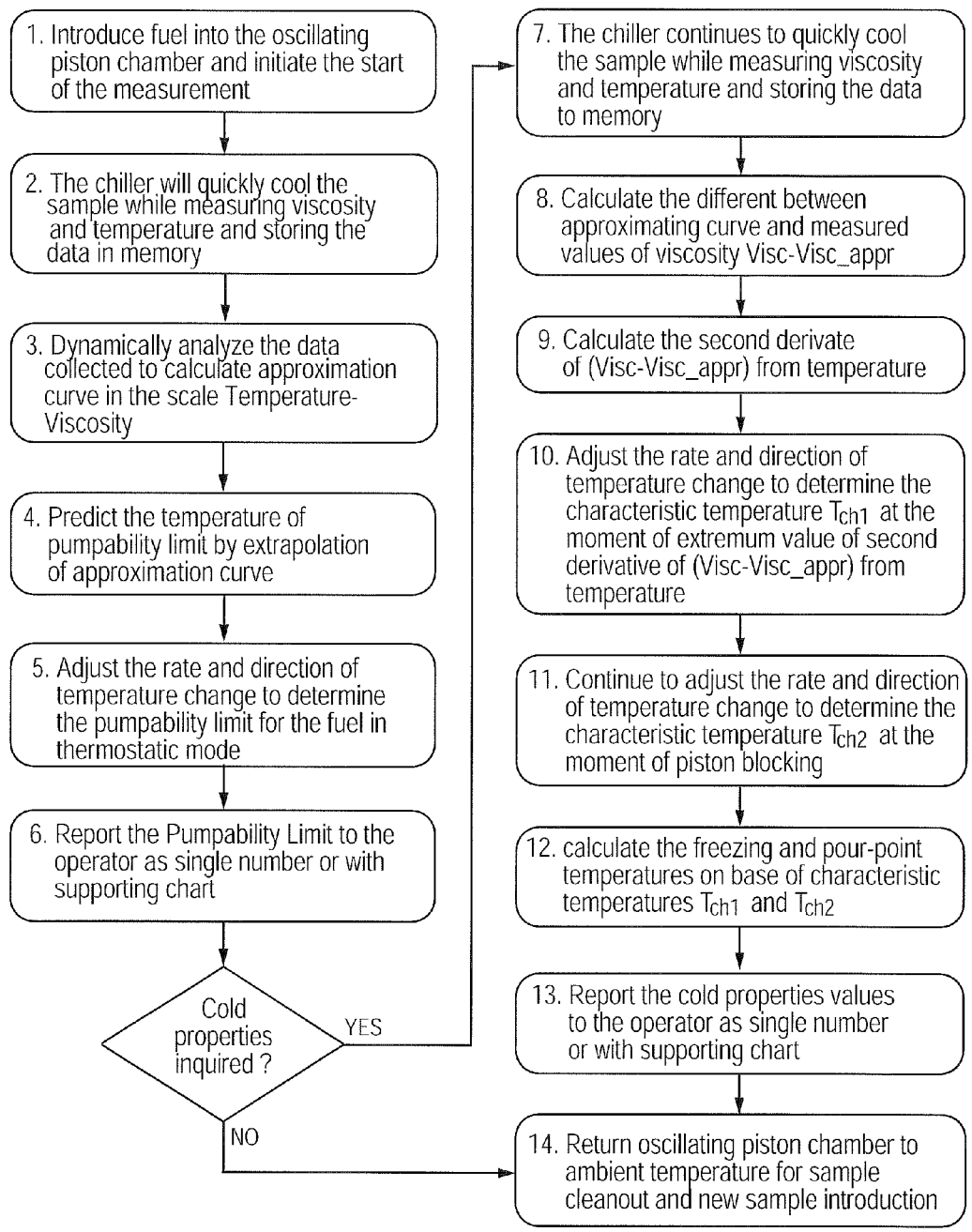
FIG. 8 is a functional block diagram used in a viscometer with a chiller to determine the pumpability limit, the freeze point and/or the pour point of a fluid.

Thereafter, as is indicated in Stage 14 of FIG. 8, the oscillating piston chamber 32 is returned to ambient temperature and the sample under test is cleaned out. Thereafter, a new sample may be introduced for a new test.

Figure 6:
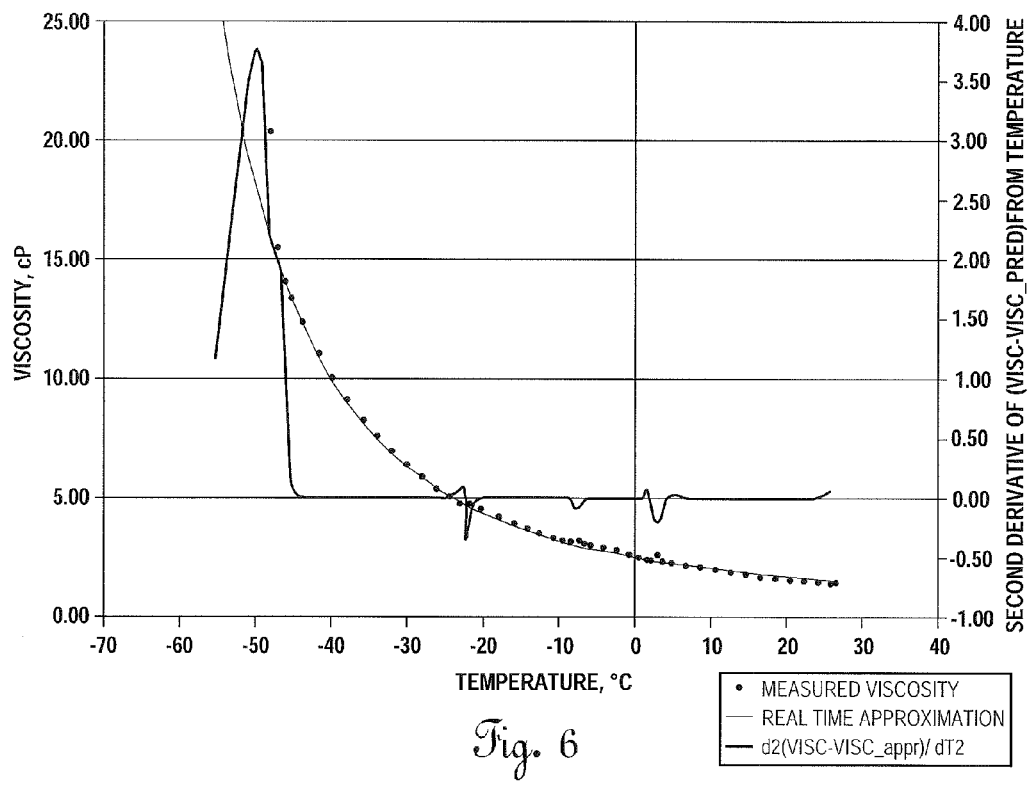
FIG. 6 is a plot of the measured viscosity versus the real time approximation of the viscosity along with the second derivative of the viscosity.

In FIG. 6, the plots are reversed with the temperature being on the bottom in reverse order from FIG. 5 so that the colder temperatures are to the left and the viscosity is on the right. A plot of dots shows the measured viscosity versus temperature with a lighter line showing the real time approximation of the viscosity. The real time approximation of viscosity closely follows the measured viscosity until the temperature gets very cold approaching minus 50° C. By calculating the second derivative of viscosity, the point at which the approximated viscosity varies from the measured viscosity becomes easily distinguished and can be used to determine pour point and freeze point.

During Stage 3 of the process as shown in FIGS. 5 and 8, the sample is dynamically analyzed from the collected data to calculate the approximation curve for the temperature/viscosity.

The real-time analysis of data during Stage 3 consist from approximation of experimental data by the function:

$$Visc = a0 \cdot \exp\left(\frac{a1}{T + a2}\right)$$

where

Visc—measured viscosity at temperature T a0, a1 and a2—the coefficients of approximation which can be obtained by least-squares method. Discussion of the least squares method can be found in standard textbooks such as Adi, H., Valentin, D., Edelman, B. E. (1999) *Neural Networks,* Thousand Oaks: Sage and references cited therein, or Neil Salkind (Ed) (2007) *Encyclopedia of Measurements and Statistics,* Thousand Oaks (Calif.): Sage.

As a result, the temperature of the pumpability limit can be predicted at Stage 4 by inverse function:

$$T_{pl}^{pred} = \frac{a1}{\ln(Visc_{lim}/a_0)} - a2$$

where Visc$_{lim}$—the viscosity of pumpability limit;

$T_{pl}^{pred}$—expected value of pumpability limit temperature in base of function extrapolation.

The knowledge of $T_{pl}^{pred}$ allows to quickly cool down the sample to expected temperature and realize the precise measurement of pumpability limit in thermostatic mode during Stage 5.

In case of cooling continuation during Stage 7, the measurement for cold properties can be realized.

The error of viscosity approximation can be calculated as (Visc−Visc$_{appr}$) during Stage 8. The quality of viscosity approximation decreases at the moment of first crystal appearances, and error (Visc−Visc$_{appr}$) sharply increases. The amount of maximal rate of error increasing can be determined from maximum of second derivative $$\frac{d^2(Visc - Visc_{appr})}{dT^2}$$

which is calculated by graphic method from measured data in real time during Stage 9. This moment corresponds to characteristic temperature $T_{ch1}$ defined during Stage 10 (see FIG. 6).

Further decreasing of temperature during Stage 11 leads to blocking of oscillating piston 30. The characteristic temperature $T_{ch2}$ is defined at this moment.

The correlation to standard values of Freeze-Point and Pour-Point can be realized on base of temperatures $T_{ch1}$ and $T_{ch2}$ and predefined correlation.

After the pumpability limit has been determined, if the cold properties of the fluid being tested are desired, then as indicated in FIG. 8, the chiller 12 continues to quickly cool the sample while measuring viscosity and temperature. In Stage 8, the difference between the approximated curve and the measured values are calculated using the least squares method. In Stage 10, the rate and direction of temperature change is continued to determine the characteristic temperature $T_{ch1}$ at the moment of deviation from the approximated temperature using the least squares.

In Stage 11, the rate and direction of the temperature change is adjusted to determine the characteristic temperature $T_{ch2}$ at the moment the oscillating piston 30 is blocked. From that moment of blocking the oscillating piston 30 in Stage 12, the freeze point and the pour point temperatures can be calculated based on the characteristic temperatures $T_{ch1}$ and $T_{ch2}$.

Figure 7:
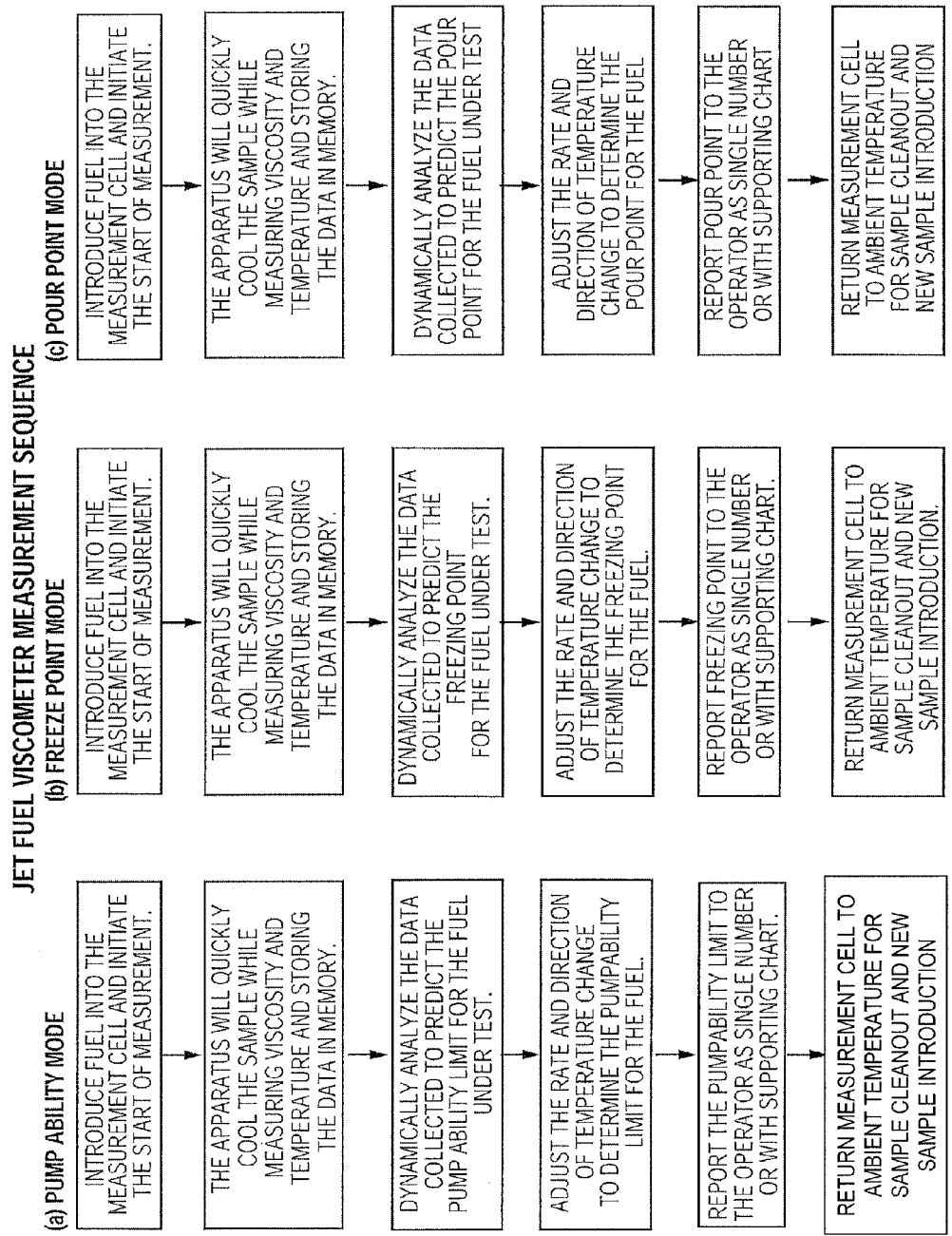
FIG. 7 is a series of block diagrams showing the determination of the pumpability mode, freeze point mode and pour point mode of a jet fuel.

While FIG. 8 shows the determination of pumpability, freeze point and pour point all in one sequence, they can be determined by separate sequences as is shown in FIG. 7(a) pumpability mode, (b) freeze point mode, or (c) pour point mode. Each of the modes 7(a), 7(b) or 7(c) are the same until the fourth step, where the rate and direction of temperature changes are used to determine pumpability limit, freeze point, or pour point.

In determining the line in FIG. 5, labeled Visc−Visc$_{appr}$, a measurement is taken. Then, the next point is approximated. The approximation is stored and then the actual measurement taken. The difference between those two is what is shown in the line Visc−Visc$_{appr}$, which is a straight line until at Stage 8. At that point, the least squares error is much greater because the difference between the predicted viscosity and the actual viscosity curve increases sharply. At this point, the viscosity in the chart is roughly 15 Centipoise and the temperature is roughly −50° C. This behavior is attributed to the formation of crystals in the fluid under test. Jet fuel at that temperature could not be used because the crystals would impede flow. The temperature at which the formation of crystals is detected is used to determine the pour point and freeze point for the fuel.

The chiller 12 may be of any particular type to lower the temperature of the viscometer 10 from ambient to sub-ambient temperatures of approximately minus 50° C. Applicant has particularly found that Stirling engines manufactured by Sun Power, Inc. located in Athens, Ohio to be particularly suitable for use as the chiller 12. However, there are other suitable Stirling engines by other manufactures that may be used. The Stirling engine is very efficient and can quickly cool small samples.

We claim:

1. A method for determining characteristics of a fluid, such as jet fuel, at sub-ambient temperatures, said characteristics including a lower pumpability limit of said fluid, the method including the following steps:
   connecting an oscillating piston type viscometer to a chiller so that said chiller can rapidly cool said viscometer;
   placing a sample of said fluid in said viscometer;
   rapidly cooling said viscometer and said sample with said chiller while measuring temperature and viscosity of said sample;
   storing said temperatures and viscosities of said sample as measured;
   analyzing said temperatures and viscosities as measured to first calculate an approximate temperature/viscosity curve of said sample;
   predicting a pumpability limit of said sample by extrapolation of said approximate temperature/viscosity curve;
   continue cooling said viscometer and said sample therein;
   first determining a measured pumpability limit of said sample by measuring the temperature of said sample whereby the maximum allowable viscosity is reached;
   said chiller further continues to cool said viscometer and said sample therein while further measuring said temperatures and viscosities and further storing said temperatures and viscosities as measured;
   second calculating the difference between (a) said approximate temperature/viscosity curve of said sample and (b) said measured viscosity;
   third calculating a second derivative from the difference between (a) said approximate temperature/viscosity curve of said sample and (b) said measured temperature; and
   second determining temperature $T_{ch1}$ of said sample at a moment of extreme value change of said second derivative.

2. The method of determining characteristics of a fluid at sub-ambient temperatures as recited in claim 1 wherein said pumpability limit is reported to an operator.

3. The method of determining characteristics of a fluid at sub-ambient temperatures as recited in claim 2 including a third determining step for measuring temperature $T_{ch2}$ of said sample when said viscometer stops measuring.

4. The method of determining characteristics of a fluid at sub-ambient tempertures as recited in claim 3 including a fourth calculating step to determine pour point temperature and freeze point temperature based upon temperatures $T_{ch1}$ and $T_{ch2}$.

5. The method of determining characteristics of a fluid at sub-ambient temperatures as recited in claim 4 wherein said pour point temperature and said freeze point temperature are reported to said operator.

6. The method of determining characteristics of a fluid at sub-ambient temperatures as recited in claim 5 wherein said chiller is a Stirling engine.

7. The method of determining characteristics of a fluid at sub-ambient temperatures as recited in claim 5 wherein temperature of said viscometer is returned to ambient temperature, cleaned and the prior steps repeated for a new sample.

* * * * *